United States Patent [19] [11] 4,427,590
Allgeier et al. [45] Jan. 24, 1984

[54] TRIAZOLOBENZODIAZEPINE DERIVATIVES

[75] Inventors: Hans Allgeier, Haagen, Fed. Rep. of Germany; André Gagneux, Basel, Switzerland

[73] Assignee: Ciba-Geigy Corporation, Ardsley, N.Y.

[21] Appl. No.: 199,770

[22] Filed: Nov. 17, 1971

[30] Foreign Application Priority Data

Nov. 23, 1980 [CH] Switzerland ............... 17352/70

[51] Int. Cl.³ .................. A61K 31/55; C07D 487/04
[52] U.S. Cl. ................. 260/245.5; 260/239 BD; 260/239.3 D
[58] Field of Search .............. 260/308 R, 245.5

[56] References Cited

U.S. PATENT DOCUMENTS 3,681,343  8/1972  Hester ................. 260/239.3 T

FOREIGN PATENT DOCUMENTS 2220612  11/1972  Fed. Rep. of Germany ...... 260/308
2220615  11/1972  Fed. Rep. of Germany ...... 260/308
7205705  10/1972  Netherlands ................. 260/308

Primary Examiner—Alton D. Rollins
Attorney, Agent, or Firm—Joseph G. Kolodny

[57] ABSTRACT

Compounds of the class of 6-phenyl-4H-s-triazolo[4,3-a][1,4]benzodiazepine-1-lower alkanols, and their ethers and esters, 1-(fluoro-lower alkyl)-6-phenyl-4H-s-triazolo[4,3-a][1,4]benzodiazepines and the 5-oxides and pharmaceutically acceptable acid addition salts thereof have central depressant properties, in particular antiaggressive and anticonvulsant actions, and are active ingredients for pharmaceutical compositions. Specific embodients are 6-phenyl-8-chloro-4H-s-triazolo[4,3-a][1,4]benzodiazepine-1-methanol and 1-(fluoromethyl)6-phenyl-8-chloro-4H-s-triazolo[4,3-a][1,4]benzodiazepine.

1 Claim, No Drawings

TRIAZOLOBENZODIAZEPINE DERIVATIVES

DETAILED DESCRIPTION

The present invention relates to certain novel diazepine derivatives and oxides thereof and to the acid addition salts, particularly the pharmaceutically acceptable acid addition salts, of these azepine derivatives and oxides.

More particularly the present invention relates to diazepine derivatives having the general formula I

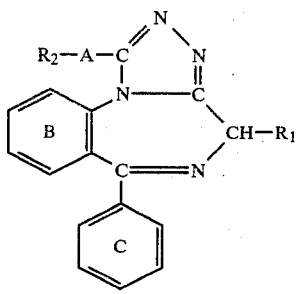

wherein
$R_1$ represents a hydrogen atom or an alkyl group having from 1 to 3 carbon atoms,
$R_2$ represents a hydroxy group, an alkoxy or an alkanoyloxy group having from 1 to 6 carbon atoms, a mono- or di-arylmethoxy group, a 2-oxacycloalkoxy group having from 5 to 7 ring members or a fluorine atom, and
A represents an alkylene group having from 1 to 3 carbon atoms
and wherein each of the rings B and C may be substituted by one or more halogen atoms up to and including the atomic number 35, trifluoromethyl groups or alkyl or alkoxy groups having from 1 to 6 carbon atoms and to their 5-oxides as well as to the acid addition salts, particularly the pharmaceutically acceptable acid addition salts, of said diazepine derivatives and of their 5-oxides.

As alkyl group in the compounds of the general formula I, $R_1$ is, e.g. the methyl, ethyl or propyl group. As the alkoxy group, $R_2$ is, e.g. the propoxy, isopropoxy, butoxy, isobutoxy, pentyloxy, isopentyloxy, hexyloxy or isohexyloxy group, preferably, however, the methoxy or ethoxy group; as the alkanoyl group, $R_2$ is, e.g. the formyloxy, acetoxy, propionoxy, butyroxy, isobutyroxy, valeroxy, isovaleroxy, pivaloyloxy, or hexanoyloxy group; and as the monoarylmethoxy group, $R_2$ is, e.g. the benzyloxy, o-, m- or p-chlorobenzyloxy, o-, m- or p-methylbenzyloxy, o-, m- or p-methoxybenzyloxy or 3,4,5-trimethoxybenzyloxy group; as the diarylmethoxy group, $R_2$ is, in particular, the diphenylmethoxy group. As the 2-oxacycloalkoxy group, $R_2$ is, e.g. the tetrahydrofuran-2-yloxy group (2-oxa-cyclopentyloxy group), the 2-oxo-cycloheptyloxy group and, in particular, the tetrahydropyran-2-yloxy group. By an alkylene group A is meant any chosen bivalent, saturated aliphatic hydrocarbop radical having 1 to 3 carbon atoms, such as the methylene, ethylidene, 1-methylethylidene, ethylene, propylene or trimethylene group; of particular importance amongst these groups is the methylene group.

Halogen atoms as substituents of the rings B and C are fluorine, chlorine or bromine atoms, whilst suitable alkyl groups or alkoxy groups having 1 to 6 carbon atoms are, e.g. methyl, ethyl, propyl, isopropyl, butyl, isobutyl, tert.butyl, pentyl, isopentyl, 2,2-dimethylpropyl, hexyl or isohexyl groups; or methoxy, ethoxy, propoxy, isopropoxy, butoxy, isobutoxy, pentyloxy, isopentyloxy, 2,2-dimethylpropoxy, hexyloxy or isohexyloxy groups. A substituent of the ring B is, in particular, in 8-position, and is preferably fluorine, bromine, the trifluoromethyl group, and especially chlorine. The ring C is preferably unsubstituted, or substituted by fluorine, chlorine or bromine in any desired position, particularly, however, by fluorine or chlorine in o-position.

The compounds of the general formula I, their 5-oxides and the corresponding pharmaceutically acceptable and addition salts possess valuable pharmacological properties. They have a central depressant action, e.g. an anticonvulsive and antiagressive action; they also inhibit somatic reflexes. The antoconvulsive effectiveness can be determined, e.g. in the electroshock test on the mouse with dosages of from ca. 2.0 mg/kg orally; in the strychnine-spasm test on the mouse with dosages of from ca. 1.5 mg/kg orally; and in the pentetrazole test on the mouse with dosages of from ca. 0.05 mg/kg orally. The antiagressive effectiveness is evident from the suppression of the fighting reaction of the mouse after oral administration of dosages of from ca. 0.3 mg/kg, whilst the general suppression of the central nervous system is shown, e.g. from the anaesthetic-potentiating action after oral administration to the mouse; as well as from observation tests. The stated and also further properties, which can be assessed by selected standard tests [cp. W. Theobald and H. A. Kunz, Arzneimittelforsch. 13, 122 (1963), as well as W. Theobald et al., Arzneimittelforsch. 17, 561 (1967)], characterise the compounds of the general formula I and their 5-oxides, as well as the pharmaceutically acceptable addition salts of the compounds of the general formula I and their 5-oxides with inorganic and organic acids, as active substances for tranquillisers and for anticonvulsants, which are applicable, e.g. for the treatment of states of tension and agitation, as well as for the treatment of epilepsy.

Of particular importance are compounds of the general formula I having hydrogen as $R_1$, the hydroxyl group as $R_2$, and an alkylene group, particularly the methylene group as A; and amongst these compounds especially those having a chlorine atom in the 8-position, particularly 6-phenyl-8-chloro-4H-s-triazolo[4,3-a][1,4]benzodiazepine-1-methanol, as well as 6-(o-fluorophenyl)- and 6-(o-chlorophenyl)-8-chloro-4H-s-triazolo[4,3-a][1,4]benzodiazepine-1-methanol. Likewise of special pharmacological importance are compounds containing hydrogen as $R_1$, fluorine as $R_2$, and the methylene group as A, especially 1-(fluoromethyl)-6-phenyl-8-chloro-4H-s-triazolo[4,3-a][1,4]benzodiazepine.

The diazepine derivatives of the general formula I their 5-oxides and the acid addition salts of these compounds generally are useful as intermediates in the production of pharmaceutically active products, and in particular such compounds having a mono- or diarylmethoxy group $R_2$ or a 2-oxacycloalkoxy group $R_2$ having 5 to 7 ring members, particularly the tetrahydropyran-2-yloxy group, are important, apart from the fact that they are themselves pharmacologically effective, as intermediates for the preparation of corresponding compounds having an hydroxyl group as $R_2$. Likewise preferred, therefore, amongst these compound types are those having hydrogen as $R_1$ and the methylene group as A, and particularly those of them in which, at the same time, ring B is substituted in 8-position by chlorine, whilst the ring C carries no substituent, or is substituted in o-position by fluorine or chlorine. 5-Oxides of compounds of the general formula I likewise have pharmacological activity, but their importance lies particularly in their applicability as intermediates for the production of further pharmacologically effective substances.

According to the present invention there is also provided a process for the production of diazipine derivatives having the general formula I but wherein $R_2$ may not represent an alkanoyloxy group, which comprises condensing the corresponding compound having the general formula II

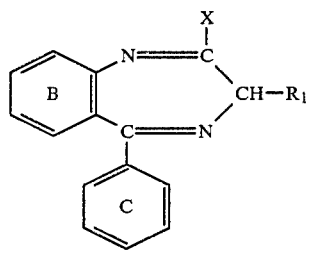

wherein
X represents a mercapto group, a lower alkoxy or a lower alkylthio group optionally activated by a substituent, or an optionally mono- or disubstituted amino group and $R_1$ has the meaning given above and the rings B and C may be substituted according to the definition given above, with a compound having the general formula III $$R_2'—A—CO—NH—NH_2 \qquad (III)$$

wherein $R_2'$ has the meaning given for $R_2$ above with the exception that it may not represent an alkanoyloxy group and A has the meaning given above.

As a lower alkylthio or alkoxy group, X is preferably the methylthio or ethylthio group, or the methoxy or ethoxy group. These groups can be activated by a substituent. Such activated groups are, e.g. the o- or p-nitrobenzylthio or the o- or p-nitrobenzyloxy group.

As a monosubstituted amino group, X is, in particular, a lower alkylamino group such as the methylamino group, or an aralkylamino group such as the benzylamino group. As a disubstituted amino group, X is, in particular, a lower dialkylamino group, such as the dimethylamino group.

The above condensation reaction is preferably performed at a reaction temperature of ca. 80° to 180° C. in an inert solvent. Suitable inert solvents are, for example, hydrocarbons such as toluene or xylene, halogenated hydrocarbons such as chlorobenzene, ethereal liquids such as diethylene glycol dimethyl ether, diethylene glycol diethyl ether or dioxane, amides, especially N,N,N',N',N'',N''-hexamethylphosphoric acid triamide, or N,N-dimethylacetamide, sulphoxides such as dimethylsulphoxide, and alcohols such as n-butanol. The reaction times are preferably between about one hour and 24 hours.

Starting materials embraced by the general formula II are described in the literature, see, amongst others, L. H. Sternbach and E. Reeder, J. Org. Chem. 26, 1111 (1961), S. C. Bell et al., J. Med. Chem. 5, 63 (1962) and G. A. Archer and L. H. Sternbach, J. Org. Chem. 29, 231 (1964). Also described are compounds embraced by the general formula III, such as, e.g. 2-benzyloxyacetic acid hydrazide and glycolic acid hydrazide [cp. Th. Curtius and N. Schwan, J. prakt. Chem. [2] 51, 364 (1895)]. Further compounds of the general formulae II and III can be produced analogously to the known compounds. For example, further starting materials of the general formula II having an optionally substituted amino group are obtained by reduction of the corresponding 4-oxides described in the literature.

According to a further aspect of the present invention there is provided a process for the production of diazepine derivatives having the general formula I wherein $R_2$ represents a hydroxy group and A represents a methylene, ethylene, trimethylene or propylene group, which comprises reducing, by means of a complex hydride in an ethereal solvent, the corresponding compound having the general formula IV

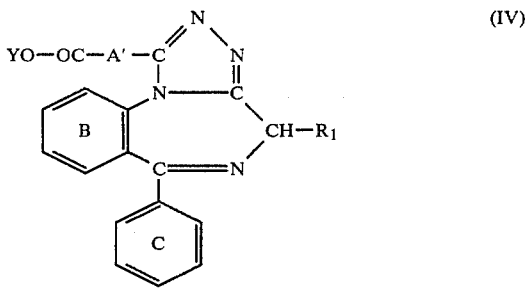

wherein
Y represents a hydrocarbon radical having at most 8 carbon atoms,
A' represents a direct bond or a methylene, ethylidene or ethylene group,
$R_1$ has the meaning given above and the rings B and C may be substituted according to the definition given above.

The complex hydride employed in this reductiom process is, e.g. lithium aluminium hydride, and the ethereal solvent, e.g. tetrahydrofuran or diethyl ether. The reduction is performed, e.g. at temperatures of between $-15°$ and $+20°$ C., preferably around ca. 0°.

Starting materials of the general formula IV can be produced analogously to the compounds of the general formula I by condensation of compounds of the general formula II with aliphatic dicarboxylic acid ester hydrazides, e.g. with oxalic acid methyl ester hydrazide or oxalic acid ethyl ester hydrazide, instead of with compounds of the general formula III.

In addition to the foregoing diazipine derivations having the formula I wherein $R_2$ represents a hydroxy group may be prepared, in accordance with the present invention, by splitting the corresponding compound having the general formula I wherein $R_2$ represents a monoarylmethoxy, diarylmethoxy or 2-oxacycloylkoxy group.

The splitting of monoarylmethoxy or diarylmethoxy groups is preferably performed with the aid of hydrochloric acid, hydriodic acid, or especially hydrobromic acid. It is advantageous to use the hydrohalic acids in a solvent. Suitable solvents are carboxylic acids such as acetic acid. The reaction temperature is ca. 20° to 150°

C. The splitting of a 2-oxacycloalkoxy group, such as, e.g. the tetrahydropyran-2-yloxy group, is effected likewise by the action of acids, such as, e.g. hydrohalic acids, but usually under milder conditions. Splitting is performed, for example, by the action of diluted aqueous hydrochloric acid to which is added a water-miscible organic solvent, such as, e.g. methanol, at temperatures of ca. 50° to 100° C. or at the boiling temperature of the reaction mixture. The starting materials for this process may be obtained e.g. according to the first described process for the production of compounds of the formula I.

Finally the present invention provides a process for the production of diazepine derivatives having the general formula I wherein $R_2$ represents an alkanoyloxy group having from 1 to 6 carbon atoms which comprises acylating the corresponding compound having the general formula I wherein $R_2$ represents a hydroxy group.

The starting materials wherein $R_2$ represents a hydroxy group may be prepared, e.g. according to any of the above described processes.

The acylation can be carried out, for example, by the reaction of the free hydroxy compounds with acid halides or acid anhydrides which are derived from aliphatic carboxylic acids having 1 to 6 carbon atoms. Acylation is performed preferably in an inert solvent, in the presence of a tertiary organic base such as, e.g. pyridine or triethylamine. Suitable as solvents are hydrocarbons such as benzene or toluene, halogenated hydrocarbons such as carbon tetrachloride or chloroform, or excess tertiary organic bases. The reaction is carried out at ca. 0° to 80° C.

The 5-oxides of the subject diazipine derivatives are prepared by oxidation of the diazipine derivative itself.

Suitable oxidising agents are preferably hydrogen peroxide or peroxy acids and the oxidation is effected e.g. at a temperature of ca. 0° to 70° C. Suitable peroxy acids are, e.g. peroxyacetic acid or benzoperoxy acids such as benzoperoxy acid or, in particular, m-chlorobenzoperoxy acid. The oxidising agents are preferably used in a solvent, e.g. peroxyacetic acid in acetic acid, and benzoperoxy acid in halogenated hydrocarbons such as methylene chloride or chloroform.

The compounds of the general formula I and their 5-oxides obtained by the processes according to the invention are optionally converted, in the usual manner, into their addition salts with inorganic or organic acids. For salt formation are used, e.g. hydrochloric acid, hydrobromic acid, sulphuric acid, phosphoric acid, perchloric acid, methanesulphonic acid, ethanesulphonic acid or citric acid, preferably in the presence of a solvent such as, e.g. acetone, methanol, ethanol, ether, or mixtures thereof.

The compounds of the general formula I as well as their 5-oxides, and the corresponding pharmaceutically acceptable acid addition salts, are preferably administered orally or rectally. The daily dosages very between 0.01 and 2 mg/kg for warm-blooded animals. Suitable dosage units, such as dragées, tablets or suppositories, preferably contain 0.5–25 mg of an active substance according to the invention, i.e. of a compound of the general formula I, of the 5-oxide thereof, or of a pharmaceutically acceptable acid addition salt of these substances. The said dosage units are prepared by the combination of the active substance with solid pulverulent carriers such as lactose, saccharose, sorbitol, mannitol; starches such as potato starch, maize starch or amylopectin, also laminaria powder or citrus pulp powder; cellulose derivatives or gelatine, optionally with the addition of lubricants such as magnesium stearate or calcium stearate, or polyethylene glycols, to form tablets or dragée cores. The latter are coated e.g. with concentrated sugar solutions which may also contain, e.g. gum arabic, talcum and/or titanium dioxide, or with a lacquer dissolved in readily volatile organic solvents or solvent mixtures. Dyestuffs can be added to these coatings, e.g. for identification of the various dosages of active substance. Further suitable dosage units for oral administration are hard gelatine capsules, as well as soft closed capsules made from gelatine and a softener such as glycerin. The former contain the active substance preferably as a granulate in admixture with lubricants such as talcum or magnesium stearate, and, optionally, stabilisers such as sodium metabisulphite or ascorbic acid.

The following directions serve to further illustrate the production of tablets, dragées and suppositories:

(a) An amount of 50.0 g of 6-phenyl-8-chloro-4H-s-triazolo[4,3-a][1,4]benzodiazepine-1-methanol is mixed with 550 g of lactose and 292 g of potato starch; the mixture is moistened with an alcoholic solution of 8 g of gelatine, and granulated through a sieve. After the drying of the granulate, 60 g of potato starch, 60 g of talcum, 10 g of magnesium stearate and 20 g of highly dispersed silicon dioxide are mixed in, and the obtained mixture is pressed to form 10,000 tablets each weighing 105 mg, and each containing 5 mg of active substance. If required, the tablets can be provided with grooves to give a more precise adjustment of the dosage amount.

(b) An amount of 2.5 g of 6-phenyl-8-chloro-4H-s-triazolo[4,3-a][1,4]benzodiazepine-1-methanol is well mixed with 16 g of maize starch and 6 g of highly dispersed silicon dioxide; the mixture is then moistened with a solution of 2 g of stearic acid, 6 g of ethylcellulose and 6 g of stearin in ca. 70 ml of isopropyl alcohol, and the whole granulated through a sieve III (Ph.Helv. V). The granulate is dried for ca. 14 hours, and then put through sieve III–IIIa. It is afterwards mixed with 16 g of maize starch, 16 g of talcum and 2 g of magnesium stearate, and the mixture pressed to obtain 1000 dragee cores. These are coated with a concentrated syrup of 2 g of lacca, 7.5 g of gum arabic, 0.15 g of dyestuff, 2 g of highly dispersed silicon dioxide, 25 g of talcum and 53.35 g of sugar, and then dried. The obtained dragees each weigh 162.5 mg and each contain 2.5 mg of active substance.

(c) 10 g of 6-phenyl-8-chloro-4H-s-triazolo[4,3-a][1,4]-benzodiazepine-1-methanol and 1990 g of finely ground suppository foundation material (e.g. cocoa butter) are thoroughly mixed and then melted. 1000 Suppositories each weighing 2 g are poured from the melt maintained homogeneous by stirring. The suppositories each contain 10 mg of active substance.

It is also possible to use as the active substance for tablets, dragées and suppositories the same amounts of 6-(o-fluorophenyl)-8-chloro-4H-s-triazolo[4,3-a][1,4]benzodiazepine-1-methanol.

In accordance with the foregoing the present invention provides in a final aspect, pharmaceutical compositions comprising a diazipine derivative, 5-oxide or pharmaceutically acceptable acid addition salt according to the invention together with a pharmaceutically acceptable diluent or carrier therefore.

The following examples further illustrate the production of the new compounds of the general formula I as

EXAMPLE 1

(a) A solution of 30 g of 2-(methylthio)-5-phenyl-7-chloro-3H-1,4-benzodiazepine [cp. G. A. Archer et al., J.Org.Chem. 29, 231 (1964)] and 19.8 g of 2-benzyloxyacetic acid hydrazide [cp. Th. Curtius and N. Schwan, J.prakt. Chem. [2] 51, 353 (1895)] in 160 ml of hexamethylphosphoric acid triamide is heated for 8 hours at 140°. The solvent is then distilled off in vacuo, and the residue distributed between methylene chloride and water. The organic phase is separated, washed with saturated aqueous sodium chloride solution, dried over sodium sulphate, and concentrated by evaporation. 1-(Benzyloxymethyl)-6-phenyl-8-chloro-4H-s-triazolo[3,4-a][1,4]benzodiazepine crystallises out; it melts at 163°–165°.

(b) In an analogous manner is obtained, with the use of 26.6 g of 2-(methylthio)-5-phenyl-3H-1,4-benzodiazepine: 1-(benzyloxymethyl)-6-phenyl-4H-s-triazolo[4,3-a][1,4]benzodiazepine, M.P. 167°–168° (from ethyl acetate/petroleum ether).

EXAMPLE 2

(a) A solution of 7.8 g of 2-(methylthio)-5-phenyl-7-chloro-3H-1,4-benzodiazepine and 3.5 g of hydracrylic acid hydrazide in 70 ml of abs. hexamethylphosphoric acid triamide is heated for 9 hours at 140° C. The solvent is then distilled off in vacuo. The residue is taken up in methylene chloride; the methylene chloride solution is washed with water and then with saturated sodium chloride solution, dried over sodium sulphate, and concentrated by evaporation. The residue is crystallised from methylene chloride/ethyl acetate/petroleum ether, and 6-phenyl-8-chloro-4H-s-triazolo[4,3-a][1,4]benzodiazepine-1-ethanol, M.P. 227°–231°, is obtained.

If, instead of hydracrylic acid hydrazide, 6.5 g of 3-benzyloxypropionic acid hydrazide are used, and the crude product is then purified by chromatography on aluminium oxide (eluting agent:ethyl acetate), and subsequent crystallisation from ethyl acetate/petroleum ether, then 1-(2-benzyloxyethyl)-6-phenyl-8-chloro-4H-s-triazolo[4,3-a][1,4]benzodiazepine, M.P. 115°–117°, is obtained.

(b) An amount of 96.5 g of 3-benzyloxypropionic acid methyl ester [cp. J. J. Bloomfield, J.Org.Chem. 27, 2742 (1962)] is dissolved in 1000 ml of abs. ethanol; to the solution are then added 49.6 g of hydrazine hydrate, and the whole is allowed to stand for 65 hours at 25°. The reaction mixture is then concentrated in vacuo, the residue distilled at ca. 150°/0.005 Torr, and 3-benzyloxypropionic acid hydrazide obtained as colourless oil.

An amount of 16.7 g of 3-benzyloxypropionic acid hydrazide is dissolved in 200 ml of abs. ethanol; the solution is then hydrogenated, after the addition of 2.0 g of palladium charcoal catalyst (5% Pd), at 20°–25° and 760 Torr for 61 hours. The reaction mixture is afterwards filtered through kieselguhr, and the filtrate concentrated by evaporation to ca. 50 ml. After the addition of petroleum ether, hydracrylic acid hydrazide precipitates and is filtered off, M.P. 94°–95°.

EXAMPLE 3

A solution of 10.0 g of 2-(methylthio)-5-phenyl-7-chloro-3H-1,4-benzodiazepine and 4.85 g of 2-methoxyacetic acid hydrazide (cp. E. J. Browne and J. B. Polya, J.Chem.Soc. 1962, 5149–5152) in 70 ml of abs. hexamethylphosphoric acid triamide is heaated for 11 hours at 140°. The solvent is then distilled off in vacuo. The residue is taken up in methylene chloride; the solution is washed with water and then with saturated sodium chloride solution, dried over sodium sulphate, and concentrated by evaporation. Crystallisation of the concentration residue from ethyl acetate/petroleum ether yields 1-(methoxymethyl)-6-phenyl-8-chloro-4H-s-triazolo[4,3-a][1,4]benzodiazepine, M.P. 185°–191°. After chromatography of the mother liquor on 100 g of silica gel "Merck", a further amount of final product of the same melting point can be isolated.

In an analogous manner is obtained, with the use of 5.5 g of 2-ethoxyacetic acid hydrazide [cp. Curtius, J.prakt. Chem. [2] 95, 171 (1917)]: 1-(ethoxymethyl)-6-phenyl-8-chloro-4H-s-triazolo[4,3-a][1,4]benzodiazepine, M.P. 161°–165° (from ethyl acetate/petroleum ether).

In an analogous manner is likewise obtained, by reaction, with 9 hours' reaction time, of 8.95 g of 2-(methylthio)-5-phenyl-3H-1,4-benzodiazepine and 4.85 g of 2-methoxyacetic acid hydrazide: 1-(methoxymethyl)-6-phenyl-4H-s-triazolo[4,3-a][1,4]benzodiazepine, M.P. 153°–154° (from ethyl acetate/petroleum ether).

EXAMPLE 4

(a) A solution of 6.0 g of 2-(methylthio)-5-phenyl-7-chloro-3H-1,4-benzodiazepine and 3.44 g of 3-ethoxypropionic acid hydrazide in 60 ml of abs. hexamethylphosphoric acid triamide is heated for 5 hours at 140°. After processing analogous to that described in Example 1 and crystallisation from ethyl acetate/petroleum ether, 1-(2-ethoxyethyl)-6-phenyl-8-chloro-4H-s-triazolo[4,3-a][1,4]benzodiazepine, M.P. 128°–132°, is obtained.

The 3-ethoxypropionic acid hydrazide used as starting material is prepared as follows:

(b) An amount of 30 g of 3-ethoxypropionic acid methyl ester [cp. C. E. Rehberg et al., J.Am.Chem.Soc. 68, 544–546 (1946)] is dissolved in 800 ml of abs. ethanol; to this solution are then added 22.7 g of hydrazine-hydrate, and the whole is allowed to stand for 3 days at 25°. The reaction mixture is concentrated in vacuo, and the residue distilled in a bulb tube at 120°/10$^{-3}$ Torr. In this manner is obtained colourless 3-ethoxypropionic acid hydrazide, M.P. 34°.

EXAMPLE 5

(a) A solution of 15,0 g 2-(methylthio)-5-phenyl-7-chloro-3H-1,4-benzodiazepine [cf. G. A. Archer et al., J. Org. Chem. 29, 231 (1964)] and 11,5 g 2-(p-methoxybenzyloxy)-acetic acid-hydrazide in 100 ml hexamethyl-phosphoric acid triamide is heated for 10 hours at 140°. The reaction mixture is worked up analogously to Example 1. The crude product is crystallised from ethyl acetate-petrol ether, whereby 1-[(p-methoxybenzyloxy)-methyl]-6-phenyl-8-chloro-4H-s-triazolo[4,3-a][1,4]benzodiazepine M.P. 157°–159° is obtained.

Analogously is obtained on using 16,7 g 2-(methylthio)-5-(o-chlorophenyl)-7-chloro-3H-1,4-benzodiazepine, 1-[(p-methoxybenzyloxy)-methyl]-6-(o-chlorophenyl)-

8-chloro-4H-s-triazolo[4,3-a][1,4]benzodiazepine M.P. 200°–203° from ethyl acetate).

Also analogously, but with a reaction time of 14 hours, there are obtained on using 15,9 g 2-(methylthio)-5-(o-fluorophenyl)-7-chloro-3H-1,4-benzodiazepine 1-[(p-methoxybenzyloxy)methyl]-6-(o-fluorophenyl)-8-chloro-4H-s-triazole[4,3-a][1,4]benzodiazepine M.P. 163,5°–165° from ethyl acetate-petrol ether);

on using 14,0 g 2-(methylthio)-5-phenyl-7-methyl-3H-1,4-benzodiazepine 1-[(p-methoxybenzyloxy)-methyl]-6-phenyl-8-methyl-4H-s-triazolo[4,3-a][1,4]benzodiazepine;

on using 17,3 g 2-(methylthio)-5-phenyl-7-bromo-3H-1,4-benzodiazepine 1-[(p-methoxybenzyloxy)-methyl]-6-phenyl-8-bromo-4H-s-triazolo[4,3-a][1,4]benzodiazepine, and on using 16,5 g 2-(methylthio)-5-(o-methoxyphenyl)-7-chloro-3H-1,4-benzodiazepine 1-[(p-methoxybenzyloxy)methyl]-6-(o-methoxyphenyl)-8-chloro-4H-s-triazolo[4,3-a][1,4]benzodiazepine.

The substituted 2-(methylthio)-5-phenyl-3H-1,4-benzodiazepines required as starting compounds for the above-named end products can be prepared from the corresponding substituted 1,3-dihydro-5-phenyl-2H-1,4-benzodiazepine-2-thiones described in J.Org.Chem. 29, analogously to the preparation of 2-(methylthio)-5-phenyl-7-chloro-3H-1,4-benzodiazepine which is described therein.

Further, there are obtained analogously to the above example, with a reaction time of 14 hours, from 14,2 g 2-(methylthio)-5-phenyl-7-fluoro-3H-1,4-benzodiazepine 1-[(p-methoxybenzyloxy)-methyl]-6-phenyl-8-fluoro-4H-s-triazolo[4,3-a][1,4]benzodiazepine;

from 15,7 g 2-(methylthio)-5-(o-tolyl)-7-chloro-3H-1,4-benzodiazepine 1-[(p-methoxybenzyloxy)-methyl]-6-(o-tolyl)-8-chloro-4H-s-triazolo[4,3-a][1,4]benzodiazepine;

from 14,8 g 2-(methylthio)-5-phenyl-7-methoxy-3H-1,4-benzodiazepine 1-[(p-methoxybenzyloxy)-methyl]-6-phenyl-8-methoxy-4H-s-triazolo[4,3-a][1,4]benzodiazepine;

from 16,7 g 2-(methylthio)-5-phenyl-7-(trifluoromethyl)-3H-1,4-benzodiazepine 1-[(p-methoxbenzyloxy)-methyl]-6-phenyl-8-(trifluoromethyl)-4H-s-triazolo[4,3-a][1,4]benzodiazepine, from 16,7 g 2-(methylthio)-5-(α,α,α-trifluoro-o-tolyl)-3H-1,4-benzodiazepine 1-[(p-methoxybenzyloxy)-methyl]-6-(α,α,α-trifluoro-o-tolyl)-4H-s-triazolo[4,3-a][1,4]benzodiazepine;

from 20,1 g 2-(methylthio)-5-(α,α,α-trifluoro-o-tolyl)-7-(trifluoromethyl)-3H-1,4-benzodiazepine 1-[(p-methoxybenzyloxy)methyl]-6-(α,α,α-trifluoro-o-tolyl)-8-(trifluoromethyl)-4H-s-triazolo[4,3-a][1,4]benzodiazepine, and from 18,4 g 2-(methylthio)-5-(α,α,α-trifluoro-o-tolyl)-7-chloro-3H-1,4-benzodiazepine 1-[(p-methoxybenzyloxy)-methyl]-6-(α,α,α-trifluoro-o-tolyl)-8-chloro-4H-s-triazolo[4,3-a][1,4]benzodiazepine.

(b) The substituted 2-(methylthio)-5-phenyl-3H-1,4-benzodiazepines used as starting compounds are obtained from the correspondingly substituted 1,3-dihydro-5-phenyl-2H-1,4-benzodiazepin-2-ones, whereof whose compounds which contain a trifluoromethyl group are described in the U.S. Pat. No. 3,341,392 and, partly also in Helv.Chim. Acta 45, 2226 (1962). The three other compounds are described in J.Org.Chem. 27,3788 (1962). These compounds are converted into the corresponding 2-thiones and the latter are reacted with dimethyl sulphate in methanolic sodium hydroxic solution analogously to the process described in J.Org.-Chem. 28, 231 (1964).

(c) 2-(p-Methoxybenzyloxy)-acetic acid hydrazide, used in all cases as second reaction component, is obtained by reacting 58 g 2-(p-methoxybenzyloxy)-acetic acid ethyl ester [cf. A. Viout and H. Gault, Compt.rend. 237, 1162 (1953)] with 22,7 g hydrazine hydrate analogously to Example 4b).

EXAMPLE 6

A solution of 1,5 g 2-(methylamino)-5-phenyl-7-chloro-3H-1,4-benzodiazepine [cf. L. H. Sternbach et al. J.Org.Chem. 26, 1111 (1961)] and 2 g of 2-benzyloxy-acetic acid hydrazide in 10 ml abs. hexamethyl-phosphoric acid triamide is heated 24 hours at 160° and a further 4 hours at 170°. Then, the reaction mixture is evaporated in vacuo and the residue is distributed between ethyl acetate and water. The organic phase is separated, washed with saturated aqueous sodium chloride solution dried over sodium sulphate and evaporated. Chromatography of the residue on silica gel, using ethyl acetate-isopropanol (7:1) as eluent and crystallisation from ethyl acetate-ether-petrol ether yields 1-(benzyloxymethyl)-6-phenyl-8-chloro-4H-s-triazolo[4,3-a][1,4]benzodiazine, M.P. 163°–165°.

Analogously, the same product is obtained on using the following starting compounds instead of 2-(methylamino)-5-phenyl-7-chloro-3H-1,4-benzodiazepine:

1,44 g 2-Amino-5-phenyl-7-chloro-3H-1,4-benzodiazepine [cf. S. C. Bell et al., J. Med.Chem. 5, 63 (1962)] or 1,90 g 2-(benzylamino)-5-phenyl-7-chloro-3H-1,4-benzodiazepine [obtainable according to British Patent Specification 1,023,793 or from the 4-oxide described by S. C. Bell et al., loc.cit. analogously to the method of L. H. Sternbach et al., loc.cit] or 1,56 g 2-(dimethylamino)-5-phenyl-7-chloro-3H-1,4-benzodiazepine [cf. British Patent Specification 1,023,753].

Also in an analogous manner are obtained on using 1,60 g 2-amino-5-phenyl-7-(trifluoromethyl)-3H-1,4-benzodiazepine 1-(benzyloxymethyl)-6-phenyl-8-(trifluoromethyl)-4H-s-triazolo[4,3-a][1,4]benzodiazepine, on using 1,42 g 2-amino-5-phenyl-7-methoxy-3H-1,4-benzodiazepine 1-(benzyloxymethyl)-6-phenyl-8-methoxy-4H-s-triazolo[4,3-a][1,4]benzodiazepine, and on using 1,34 g 2-amino-5-phenyl-7-methyl-3H-1,4-benzodiazepine 1-(benzyloxymethyl)-6-phenyl-8-methyl-4H-s-triazolo[4,3-a][1,4]benzodiazepine.

The three starting compounds mentioned above are obtained e.g. according to the process of deutsche Offenlegungsschrift 1.933.986, Chemical Abstracts 72, 100772 h (1970), or analogously to the 2-amino-compound named before.

EXAMPLE 7

A solution of 8.0 g of 2-(methylthio)-5-phenyl-7-chloro-3H-1,4-benzodiazepine and 1.4 g of 3-hydroxybutyric acid hydrazide [cp. J.Biol.Chem. 60, 180 (1924)] in 70 ml of abs. hexamethylphosphoric acid triamide is heated for 9 hours at 140°. After processing analogous to that described in Example 1 and crystallisation from ethyl acetate/ether, α-methyl-6-phenyl-8-chloro-4H-s-triazolo[4,3-a][1,4]benzodiazepine-1-ethanol, M.P. 182°–184°, is obtained.

With application of 4.1 g of 2-methyllactic acid hydrazide [cp. R. Metze and W. Kort, Chem.Ber. 91, 417 (1958)] is obtained, after a reaction time of 23 hours with otherwise the same procedure, α,α-dimethyl-6-phenyl-8-chloro-4H-s-triazolo[4,3-a][1,4]benzodiazepine-1-methanol, M.P. 234°–236° (from ethyl acetate/petroleum ether).

EXAMPLE 8

Crude 1-[(diphenylmethoxy)-methyl]-6-phenyl-8-chloro-4H-s-triazolo[4,3-a][1,4]benzodiazepine is obtained, analogously to Example 1, starting with 15.0 g of 2-(methylthio)-5-phenyl-7-chloro-3H-1,4-benzodiazepine and 14.1 g of 2-(diphenylmethoxy)-acetic acid hydrazide in 100 ml of hexamethylphosphoric acid triamide, the reaction time being 12 hours. The crude product is purified by chromatography on silica gel with employment of benzyene/ethyl acetate (1:1) as the eluting agent, and crystallisation of the homogeneous fractions from ethyl acetate/petroleum ether. The pure substance melts at 202°–203°.

The hydrazide required as starting material is obtained from 2-(diphenylmethoxy)-acetic acid methyl ester [cp. C. Djerassi and C. R. Scholz, J.Org.Chem. 13, 830 (1948)] and hydrazine hydrate, analogously to Example 4b), as oil.

EXAMPLE 9

From 15.0 g of 2-(methylthio)-5-phenyl-7-chloro-3H-1,4-benzodiazepine and 9.6 g of 2-(tetrahydropyran-2-yloxy)-acetic acid hydrazide in 80 ml of hexamethylphosphoric acid triamide is obtained analogously to Example 1, but with a reaction duration of 24 hours, crude 1-[(tetrahydropyran-2-yloxy)-methyl]-6-phenyl-8-chloro-4H-s-triazolo[4,3-a][1,4]benzodiazepine. This is purified by chromatography on silica gel with the use of benzene/isopropanol (95:5) as the eluting agent, and subsequent crystallisation of the homogeneous fractions from ethyl acetate/petroleum ether. The pure substance melts at 159°–161°.

The hydrazide required as starting material is produced as follows:

(a) 84 g of 3,4-dihydro-2H-pyran and 132 g of glycolic acid butyl ester are dissolved at room temperature. To this solution are added 0.5 ml of concentrated hydrochloric acid, whereupon the temperature immediately rises to 90°. The solution is cooled to room temperature and stirred for 2 hours. After the addition of 1 g of sodium bicarbonate, the crude product is distilled under 17 Torr to obtain 2-(tetrahydropyran-2-yloxy)-acetic acid butyl ester, B.P. 127°/17 Torr.

(b) 10.81 g of the above ester and 5 g of hydrazine hydrate are dissolved in 50 ml of abs. ethanol, the solution being then stirred for 20 hours at 60°. The solution is concentrated in vacuo, and the residue distilled in a ball tube. 2-(Tetrahydropyran-2-yloxy)-acetic acid hydrazide passes over under 0.08 Torr at ca. 150° and is in the form of a colourless oil, which soon crystallises, M.P. 55°–78°.

EXAMPLE 10

A solution of 8 g of 2-(methylthio)-5-phenyl-7-chloro-3H-1,4-benzodiazepine and 3.68 g of 2-fluoroacetic acid hydrazide [cp. M. A. Phillips, Agr.Vet.Chem. 2, 86–87 (1961), C. A. 57, 12314 (1962)] in 80 ml of hexamethylphosphoric acid triamide is heated for 8 hours at 140° The solvent is then distilled off in vacuo, and the residue distributed between methylene chloride and water. The organic phase is separated, washed with saturated aqueous sodium chloride solution, dried over magnesium sulphate, and concentrated by evaporation. The residue is recrystallized from ethyl acetate/petroleum ether to obtain 1-(fluoromethyl)-6-phenyl-8-chloro-4H-s-triazolo[4,3-a][1,4]benzodiazepine, M.P. 153°–154°.

EXAMPLE 11

(a) An amount of 25 g of 1-(benzyloxymethyl)-6-phenyl-8-chloro-4H-s-triazolo[4,3-a][1,4]benzodiazepine is dissolved in 200 ml of glacial acetic acid; to this solution are then added 170 ml of 48% aqueous hydrobromic acid. The mixture is heated for 90 minutes at 80°, and afterwards cooled to 5°; the pH-value of the mixture is adjusted with concentrated sodium hydroxide solution to 6, whilst stirring is maintained, and water and also methylene chloride are then added. The organic phase is separated, washed with saturated aqueous sodium chloride solution, dried over sodium sulphate, and concentrated by evaporation. The residue is dissolved in ethyl acetate/methanol (9:1), the solution filtered through a column of 150 g of silica gel (Merck ®, particle size 0.05–0.2 mm), and the column eluted with ethyl acetate/methanol (9:1) to (7:3). The eluate is concentrated by evaporation and the residue crystallised from ethyl acetate/ether. In this manner is obtained 6-phenyl-8-chloro-4H-s-triazolo [4,3-a][1,4]benzodiazepine-1-methanol, M.P. 210°–211°.

(b) In an analogous manner is obtained, starting with 5 g of 1-(benzyloxymethyl)-6-phenyl-4H-s-triazolo[4,3-a] [1,4]benzodiazepine in 40 ml of glacial acetic acid and 35 ml of 48% aqueous hydrobromic acid with a reaction time of 105 minutes: 6-phenyl-4H-s-triazolo[4,3-a][1,4] benzodiazepine-1-methanol, M.P. 205°–206° (from ethyl acetate/petroleum ether).

In a likewise analogous manner is obtained, with application of the acid amounts stated in the second paragraph and with a reaction time of 120 minutes, from 5 g of 1-(benzyloxymethyl)-6-phenyl-8-(trifluoromethyl)-3H-1,4-benzodiazepine:- 6-phenyl-8-(trifluoromethyl)-4H-s-triazolo[4,3-a][1,4]benzodiazepine-1-methanol; from 5 g of 1-(benzyloxymethyl)-6-phenyl-8-methoxy-4H-s-triazolo[4,3-a][1,4]benzodiazepine:- 6-phenyl-8-methoxy-4H-s-triazolo[4,3-a][1,4]benzodiazepine-1-methanol; and from 5 g of 1-(benzyloxymethyl)-6-phenyl-8-methyl-4H-s-triazolo[4,3-a][1,4]benzodiazepine:- 6-phenyl-8-methyl-4H-s-triazolo[4,3-a][1,4]benzodiazepine-1-methanol.

EXAMPLE 12

To a solution of 3,0 g 1-[(p-methoxybenzyloxy)-methyl]-6-phenyl-8-chloro-4H-s-triazolo[4,3-a][1,4]benzodiazepine in 30 ml of glacial acetic acid is added at 25° 24 ml 48% aqueous hydrobromic acid. The reaction mixture is stirred for 20 minutes, neutralised with 30% sodium hydroxide solution and extracted with methylenechloride. The organic phase is separated, washed with water, dried over sodium sulphate and evaporated to dryness. The crystallisation of the residue from acetate-ether-petrol ether yields 6-phenyl-8-chloro-4-H-s-triazolo[4,3-a][1,4]benzodiazepine-1-methanol, M.P. 209°–211°.

Analogously are obtained from 3,23 g 1-[(p-methoxybenzyloxy)methyl]-6-(o-chlorophenyl)-8-chloro-4H-s-triazolo[4,3-a][1,4]benzodiazepine at a reaction temperature of 20° and 55 minutes reaction time 6-(o-chlorophenyl)-8-chloro-4H-s-triazolo[4,3-a][1,4]benzodiazepine-1-methanol, M.P. 235°–237° (from ethyl acetate-petrol ether);

from 3,12 g 1-[(p-methoxybenzyloxy)-methyl]-6-(o-fluorophenyl)-8-chloro-4H-s-triazole[4,3-a][1,4]benzodiazepine at a reaction temperature of 20° and a reaction time of 15 minutes 6-(o-fluorophenyl)-8-chloro-4H-s-triazolo[4,3a][1,4]benzodiazepine-1-methanol M.P. 195°–197° (from ethyl acetate-petrol ether).

Also analogously are obtained at 20° with a reaction of 75 minutes from 2,86 g 1-[(p-methoxybenzyloxy)-methyl]-6-phenyl-8-methyl-4H-s-triazolo[4,3-a][1,4]benzodiazepine 6-phenyl-8-methyl-4H-s-triazolo[4,3-a][1,4]benzodiazepine-1-methanol;

from 3,32 g 1-[(p-methoxybenzyloxy)-methyl]-6-phenyl-8-bromo-4H-s-triazolo[4,3-a][1,4]benzodiazepine 6-phenyl-8-bromo-4H-s-triazolo[4,3-a][1,4]benzodiazepine-1-methanol;

from 3,20 g 1-[(p-methoxybenzyloxy)-methyl]-6-(o-methoxyphenyl)-8-chloro-4H-s-triazolo[4,3-a][1,4]benzodiazepine 6-(o-methoxyphenyl)-8-chloro-4H-s-triazolo[4,3-a][1,4]benzodiazepine-1-methanol;

from 3,12 g 1-[(p-methoxybenzyloxy)-methyl]-6-phenyl-8-fluoro-4H-s-triazolo[4,3-a][1,4]benzodiazepine 6-phenyl-8-fluoro-4H-s-triazolo[4,3-a][1,4]benzodiazepine-1-methanol;

from 3,10 g 1-[(p-methoxybenzyloxy)-methyl]-6-(o-tolyl)-8-chloro-4H-s-triazolo[4,3-a][1,4]benzodiazepine 6-(o-tolyl)-8-chloro-4H-s-triazolo[4,3-a][1,4]benzodiazepine-1-methanol;

from 2,98 g 1-[(p-methoxybenzyloxy)-methyl]-6-phenyl-8-methoxy-4H-s-triazolo[4,3-a][1,4]benzodiazepine 6-phenyl-8-methoxy-4H-s-triazolo[4,3-a][1,4]benzodiazepine-1-methanol;

from 3,23 g 1-[(p-methoxybenzyloxy)-methyl]-6-phenyl-8-(trifluoromethyl)-4H-s-triazolo[4,3-a][1,4]benzodiazepine 6-phenyl-8-(trifluoromethyl)-4H-s-triazolo[4,3-a][1,4]benzodiazepine-1-methanol;

from 3,23 g 1-[(p-methoxybenzyloxy)-methyl]-6-($\alpha,\alpha,\alpha$-trifluoro-o-tolyl)-4H-s-triazolo[4,3-a][1,4]benzodiazepine 6-($\alpha,\alpha,\alpha$-trifluoro-o-tolyl)-4H-s-triazolo[4,3-a][1,4]benzodiazepine-1-methanol;

from 3,70 g 1-[(p-methoxybenzyloxy)-methyl]-6-($\alpha,\alpha,\alpha$-trifluor-o-tolyl)-8-(trifluoromethyl)-4H-s-triazolo[4,3-a][1,4]benzodiazepine 6-($\alpha,\alpha,\alpha$-trifluoro-o-tolyl)-8-(trifluoromethyl)-4H-s-triazolo[4,3-a][1,4]benzodiazepine-1-methanol, and from 3,46 g 1-[(p-methoxybenzyloxy)-methyl]-6-($\alpha,\alpha,\alpha$-trifluoro-o-tolyl)-8-chloro-4H-s-triazolo[4,3-a][1,4]benzodiazepine 6-($\alpha,\alpha,\alpha$-trifluoro-tolyl)-8-chloro-4H-s-triazolo[4,3-a][1,4]benzodiazepine-1-methanol.

EXAMPLE 13

A solution of 100 mg of 1-[(diphenylmethoxy)-methyl]-6-phenyl-8-chloro-4H-s-triazolo[4,3-a][1,4]benzodiazepine in 10 ml of glacial acetic acid and 8 ml of 48% hydrobromic acid is stirred for 45 minutes at 25°. The reaction mixture is then neutralised with 30% aqueous sodium hydroxide solution, and extracted with ethyl acetate. The organic phase is washed with saturated sodium chloride solution, dried over sodium sulphate, and concentrated by evaporation. Crystallisation of the residue from ethyl acetate/ether/petroleum ether yields: 6-phenyl-8-chloro-4H-s-triazolo[4,3-a][1,4]benzodiazepine-1-methanol, M.P. 210°–211°.

EXAMPLE 14

An amount of 10 ml of 1-n hydrochloric acid is added to a solution of 200 mg of 1-[(tetrahydrofuran-2-yloxy)-methyl]-6-phenyl-8-chloro-4H-s-triazolo[4,3-a][1,4]-benzodiazepine in 3 ml of methanol; the whole is then stirred for 1½ hours at 70°–80°. The reaction mixture is diluted with ethyl acetate, and extracted with aqueous sodium bicarbonate solution. The organic phase is washed with water and saturated sodium chloride solution, dried over sodium sulphate, and concentrated by evaporation. Crystallisation of the residue from ethyl acetate/ethyl/petroleum ether yields: 6-phenyl-8-chloro-4H-s-triazolo [4,3-a][1,4]benzodiazepine-1-methanol, M.P. 210°–211°.

EXAMPLE 15

An amount of 7.0 g of 6-phenyl-8-chloro-4H-s-triazolo[4,3-a][1,4]benzodiazepine-1-methanol is dissolved in 50 ml of absolute pyridine; to the solution are added 2.4 ml of acetic anhydride, and the whole is then allowed to stand for 17 hours at 25°. The reaction mixture is afterwards concentrated in vacuo. The residue is dissolved in methylene chloride, and the solution washed with water and saturated sodium chloride solution, dried over sodium sulphate, and concentrated by evaporation. After crystallisation of the residue from ethyl/acetate is obtained 1-(acetoxymethyl)-6-phenyl-8-chloro-4H-s-triazolo[4,3-a][1,4]benzodiazepine, M.P. 210°–212°.

In an analogous manner are obtained:
with application of 7.44 g of 6-(o-fluorophenyl)-8-chloro-4H-s-triazolo[4,3-a][1,4]benzodiazepine-1-methanol: 1-(acetoxymethyl)-6-(o-fluorophenyl)-8-chloro-4H-s-triazolo[4,3-a][1,4]benzodiazepine; and
with application of 7.74 g of 6-(o-chlorophenyl)-8-chloro-4H-s-triazolo[4,3-a][1,4]benzodiazepine-1-methanol: 1-(acetoxymethyl)-6-(o-chlorophenyl)-8-chloro-4H-s-triazolo[4,3-a][1,4]benzodiazepine.

EXAMPLE 16

A solution of 3.11 g of m-chloroperoxybenzoic acid in 40 ml of methylene chloride is added dropwise at 0°–5° in the course of 10 minutes, with stirring, to a solution of 3.0 g of 6-phenyl-8-chloro-4H-s-triazolo [4,3-a][1,4]benzodiazepine-1-methanol in 80 ml of methylene chloride. The reaction mixture is stirred, in a melting ice bath, for a further 16 hours. It is then concentrated in vacuo, and to it are added ether and petroleum ether. The precipitated crystals are filtered off under suction, and recrystallised twice from methanol/ethyl acetate/ether. The obtained 6-phenyl-8-chloro-4H-s-triazolo[4,3-a][1,4]benzodiazepine-1-methanol-5-oxide melts at 267°–269°.

The following are obtained in an analogous manner:
starting with 3.84 g of 1-(benzyloxymethyl)-6-phenyl-8-chloro-4H-s-triazolo[4,3-a][1,4]benzodiazepine is obtained:
1-(benzyloxymethyl)-6-phenyl-8-chloro-4H-s-triazolo [4,3-a][1,4]benzodiazepine-5-oxide, M.P. 189°–193° (from ether);
starting with 3.13 g of 1-(methoxymethyl)-6-phenyl-8-chloro-4H-s-triazolo[4,3-a][1,4]benzodiazepine is obtained: 1-(methoxymethyl)-6-phenyl-8-chloro-4H-s-triazolo[4,3-a][1,4]benzodiazepine-5-oxide, M.P. 244°–248° (from dioxane);

starting with 3.16 g of 6-(o-fluorophenyl)-8-chloro-4H-s-triazolo[4,3-a][1,4]benzodiazepine-1-methanol is obtained:
6-(o-fluorophenyl)-8-chloro-4H-s-triazolo[4,3-a][1,4]benzodiazepine-1-methanol-5-oxide; and
starting with 3.32 g of 6-(o-chlorophenyl)-8-chloro-4H-s-triazolo[4,3-a][1,4]benzodiazepine-1-methanol is obtained: 6-(o-chlorophenyl)-8-chloro-4H-s-triazolo[4,3][1,4]benzodiazepine-1-methanol-5-oxide.

EXAMPLE 17

(a) A solution of 0.37 g of 6-phenyl-8-chloro-4H-s-triazolo[4,3-a][1,4]benzodiazepine-1-carboxylic acid ethyl ester in 5 ml of absolute tetrahydrofuran is added dropwise in the course of 15 minutes, with ice cooling and with stirring, to a suspension of 0.078 g of lithium aluminium hydride in 5 ml of absolute tetrahydrofuran. After a further 45 minutes of stirring at 0°-5°, 0.40 ml of 1-n sodium hydroxide solution are added dropwise. The inorganic salts are filtered off, the filtrate is concentrated in vacuo, and the residue dissolved in 10 ml of chloroform. The solution is washed with 1-n sodium hydroxide solution and then with water, dried over sodium sulphate, and concentrated by evaporation. The residue is recrystallised from ethyl acetate/petroleum ether to obtain 6-phenyl-8-chloro-4H-s-triazolo[4,3-a][1,4benzodiazepine-1-methanol, M.P. 210°-211°.

The following are obtained in an analogous manner:
from 0.33 g of 6-phenyl-4H-s-triazolo[4,3-a][1,4]benzodiazepine-1-carboxylic acid ethyl ester is obtained: 6-phenyl-4H-s-triazolo[4,3-a][1,4]benzodiazepine-1-methanol, M.P. 205°-206° (from ethyl acetate/petroleum ether);
from 0.38 g of 6-(o-fluorophenyl)-4H-s-triazolo[4,3-a][1,4]benzodiazepine-1-carboxylic acid ethyl ester is obtained: 6-(o-fluorophenyl)-4H-s-triazolo[4,3-a][1,4]benzodiazepine-1-methanol, M.P. 195°-197° (from ethyl acetate/petroleum ether); and
from 0.40 g of 6-(o-chlorophenyl)-4H-s-triazolo[4,3-a][1,4]benzodiazepine-1-carboxylic acid ethyl ester is obtained: 6-(o-chlorphenyl)-4H-s-triazolo[4,3-a][1,4]benzodiazepine-1-methanol, M.P. 235°-237° (from ethyl acetate/petroleum ether).

The ethyl ester required as starting material for the first mentioned reduction is produced as follows:

(b) A solution of 3.0 g of 2-(methylthio)-5-phenyl-7-chloro-3H-1,4-benzodiazepine [cp. G. A. Archer et al., J.Org.Chem. 29, 231 (1964)] and 4.0 g of oxalic acid monoethyl ester hydrazide in 100 ml of n-butanol is refluxed for 8 hours. The solvent is then evaporated off in vacuo, and the residue distributed between methylene chloride and water. The organic phase is separated, washed with saturated aqueous sodium chloride solution, dried with anhydrous potassium carbonate solution, and concentrated by evaporation. The residue is chromatographed on 300 g of silica gel with the use of a mixture of ethyl acetate and hexane (3:2) as solvent and eluting agent. The fractions are concentrated by evaporation, the homogeneous residues combined and recrystallised from ethyl acetate/hexane to thus obtain 6-phenyl-8-chloro-4H-s-triazolo [4,3-a][1,4]benzodiazepine-1-carboxylic acid ethyl ester, M.P. 233°-235°.

The further ethyl esters employed as starting materials are obtained in an analogous manner.

EXAMPLE 18

An amount of 0.13 ml of 70% perchloric acid is added at 25° to a solution of 0.5 g of 6-phenyl-8-chloro-4H-s-triazolo[4,3-a][1,4]benzodiazepine-1-methanol in 1 ml of methanol and 1 ml of acetone. The mixture is allowed to stand for 16 hours at 0°; the precipitated crystals are filtered off under suction, and recrystallised from methanol/acetone. The obtained 6-phenyl-8-chloro-4H-s-triazolo[4,3-a][1,4]benzodiazepine-1-methanol-perchlorate melts at 247°-250°. The crystals contain an equimolar amount of acetone.

What we claim is:
1. The compound which is 6-phenyl-8-chloro-4H-s-triazolo[4,3-a][1,4]benzodiazepine-1-methanol.

* * * * *